| (12) | United States Patent<br>Hartley | (10) Patent No.: US 8,022,366 B2<br>(45) Date of Patent: Sep. 20, 2011 |
|---|---|---|

(54) NON-INVASIVE QUALITATIVE MEASUREMENT OF CHEMISTRY OF BLOOD AND BODILY FLUIDS

(75) Inventor: Frank Hartley, Arcadia, CA (US)

(73) Assignee: Frank Hartley, Arcadia, CA (US)

( * ) Notice: Subject to any disclaimer, the term of this patent is extended or adjusted under 35 U.S.C. 154(b) by 575 days.

(21) Appl. No.: 12/157,513

(22) Filed: Jun. 11, 2008

(65) Prior Publication Data

US 2009/0242771 A1 Oct. 1, 2009

Related U.S. Application Data

(60) Provisional application No. 60/933,969, filed on Jun. 11, 2007.

(51) Int. Cl.
*G01J 5/02* (2006.01)
*G01J 5/00* (2006.01)

(52) U.S. Cl. .............. 250/340; 250/338.1; 250/339.07

(58) Field of Classification Search .............. 250/340, 250/338.1, 339.07, 339.03, 339.04; 356/222
See application file for complete search history.

(56) References Cited

U.S. PATENT DOCUMENTS 7,088,441 B2* 8/2006 Nahum et al. ............ 356/222
2002/0033453 A1* 3/2002 Sauer et al. .............. 250/338.1

* cited by examiner

*Primary Examiner* — David Porta
*Assistant Examiner* — Faye Boosalis (57) ABSTRACT

Mid-IR spectrometer with no moving parts, which is small and compact, low power consuming, and can monitor blood sugar (glucose) and other blood and bodily fluid analytes on a continuing basis. It has many applications in the health, forensic, environmental and other areas.

20 Claims, 11 Drawing Sheets

FIGURE 16 (prior art) show a mid IR spectrum for cocaine HCl;

FIGURE 17 shows a mid IR spectrum for Bilirubin ($C_{33}H_{36}N_4O_6$)

NON-INVASIVE QUALITATIVE MEASUREMENT OF CHEMISTRY OF BLOOD AND BODILY FLUIDS

The Applicant claims the benefit of the provisional patent No. 60/933,969, filed on Jun. 11, 2007.

A companion co-pending non-provisional patent application, filed Jun. 8, 2008, Ser. No. 12/157,511, is filed together with this non-provisional patent application.

FIELD OF THE INVENTION

This invention relates to a very compact mid-infrared spectrometer with a linear array of thermally activated capacitive elements and a continuous quarter-wave plate based wave filter.

This invention relates to an apparatus and method to non-invasively monitor specific blood analyte levels such as glucose, and to monitor specific bodily fluids such as saliva or urine for pathogens.

This invention relates to the simultaneous detection of multiple analytes.

This invention relates to wearable, non-invasive sensor which may form an artificial pancreas in conjunction with an insulin pump, known in the art.

BACKGROUND

Lightweight wearable sensors (finger, toe, earlobe clip-on's) have been in wide use for monitoring hospital patients for the oxygen content in their blood, non-invasively, by detecting electromagnetic radiation in the near-infrared ("near IR").

However, many chemical compounds in the blood or other bodily fluids, which are detectable analytes or detectable components of pathogens, are more clearly identified from their spectrum in the mid-infrared ("mid-IR").

The source of these spectra typically arises from molecular vibrations due to the nature of the bonds within a molecule, and mediated by the molecular structure, so that each molecular species tend to have distinct spectra. The near IR spectra of many in vivo substances, such as glucose in blood, are obscured by spectral absorption peaks or plateaus in the spectrum of the water in blood, for example. However, these spectra tend to extend into the mid infrared ("mid IR").

Typical spectrometers for the mid-IR tend to need cooling and are generally bulky and expensive, and are not suitable to be worn by a human or an animal, able to freely moving about and attending to regular business. There is a long-felt need for a wearable analyte detector which is accurate and remains in calibration.

In a molecule, the atoms are not held rigidly apart. Instead they can move, as if they are attached by a spring of equilibrium separation. See FIG. 1 (prior art). This bond can either bend or stretch. If the bond is subjected to infrared radiation of a specific frequency (between 300-4000 $cm^{-1}$), it will absorb the energy, and the bond will move from the lowest vibration state, to the next highest. In a simple diatomic molecule, there is only one direction of vibrating, stretching. This means there is only one band of infrared absorption. Weaker bonds require less energy, as if the bonds are springs of different strengths. If there are more atoms, there will be more bonds, and therefore more modes of vibrations. This will produce a more complicated spectrum. For a linear molecule with "n" atoms, there are 3n–5 (for n=2 or greater) vibration modes, if it is nonlinear, it will have 3n–6 for (n>2) modes. These resonant frequencies are determined by the shape of the molecular potential energy surfaces, the masses of the atoms and, by the associated vibronic coupling. The resonant frequencies can be, in a first approximation to a description of the molecular system, related to the strength of the bond, and the mass of the atoms at either end of it. Thus, the frequency of the vibrations can be associated with a particular bond type. Measurement of physiological concentrations of compounds in vivo in situ in blood, such as glucose ("blood sugar"), or in saliva (or other bodily fluids) by infrared (IR) absorption spectroscopy is interfered with by water (and protein) absorption spectra. The spectral absorbance of water in the mid-IR does not obscure the 900-1500 $cm^{-1}$ 'fingerprint' spectral bands and only partially obscures the 2700-3600 $cm^{-1}$ spectral bands that are rich in characteristic absorbencies.

Thus, the rich mid-IR absorption texture of organic compounds and the diversity of the absorption bands for water result in potential compound quantifications, which are significantly better than for that of the near-IR.

Bodily fluids can be similarly analyzed in the mid-IR by applying the mid-IR spectral detector-analyzer to a transparent (in the mid IR) "cell," or fluid holder, where the fluid may be a saliva sample or urine sample, for example, and which the spectral-detector clamps around, or, onto, rather than clamping around, or onto, a finger or an earlobe.

A reliable spectral analyzer, which has sufficient effective penetrative depth (by operating reliably in the mid-IR), to analyze in vivo blood glucose, or other fluid, "off-line", in a cell, is believed to not exist heretofore.

Operating as a "pathometer," a mid-IR spectral detector-analyzer, would answer a long-felt need, namely, as an apparatus, which would detect the antigenic materials or actual pathogens or pathogenic components from viruses, bacteria or pathogens from saliva, and fluid samples from ulcers or open sores after the collection of very small samples from these various sites.

Both type I and Type II diabetes are clinically controlled with insulin injections, typically taken at discrete times by pricking the skin so as to draw a droplet of blood and blotting on a paper test strip which then reads the "blood sugar" concentration and by the person with the diabetes regulating the blood sugar in vivo blood sugar concentration by discrete injections of insulin administered by hypodermic needle. There are also, known in the art, wearable insulin pumps which are typically programmed, or manually set, or by a combination of programming and manual setting set, to deliver insulation amounts on a more continuous basis into, in vivo, the bloodstream, via a pre-positioned hypodermic needle, or other means.

The "missing link" has heretofore been the glucose sensor. Although measurement of oxygenation by wearable or clip-on sensors is widely and routinely used for monitoring hospital patient, a similar application for blood sugar (glucose) has not so far blossomed. The reason is that the continuous measurement of glucose levels in the blood by a non-invasive technique requires a more subtle approach than the extrapolation of blood oxygen-level techniques by "brute force," in the scientific sense.

Figure 2:
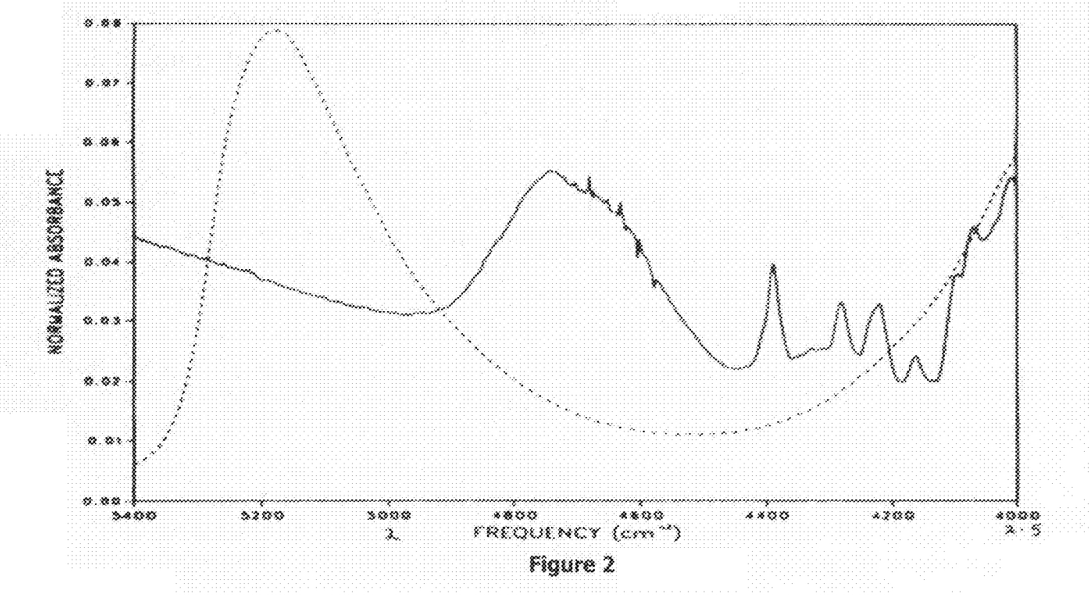
FIG. 2 (prior art) shows near-infrared spectra for glucose and 0.1 M, pH 7.2 phosphate buffer.
Figure 4:
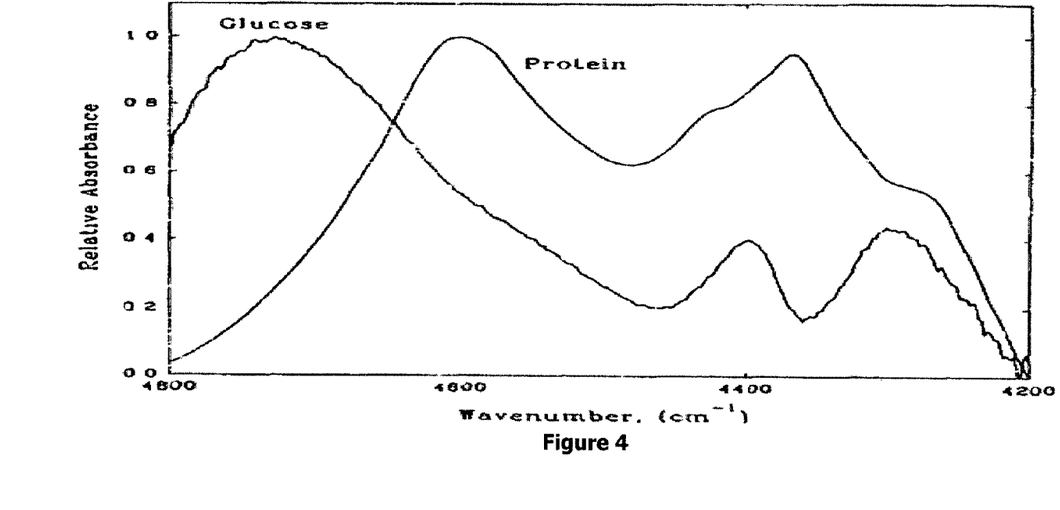
FIG. 4 (prior art) shows near-IR absorbance spectra for aqueous solutions of bovine serum albumin (66.5 g/L) and glucose (10 mM). For each case, the optical path length is 1 mm and the matrix is a pH 7.4 phosphate buffer.

Measuring physiological concentrations of glucose in blood by infrared (IR) absorption spectroscopy for glucose has concentrated on the near IR (4000-6000 $cm^{-1}$), see FIG. 2 (prior art[1]) but interference from protein and water absorption spectra has precluded univariant calibration or glucose concentrations measurements. The 2%-5% absorbance for the glucose spectral bands (FIG. 2, prior art) exaggerates the spectral diversity of the near IR. The circled portion of the IR transmission curve between 4000-4600 $cm^{-1}$ (FIG. 2, prior art[2]) puts this in perspective. In FIG. 4 (prior art), the misrepresentation is magnified by referencing relative absorbance {0-1} rather than actual absorbance (0.02-0.05). FIG. 4 (prior art) also demonstrates that these glucose absorbencies, weak though they be, are masked by protein and water absorption.

Figure 3:
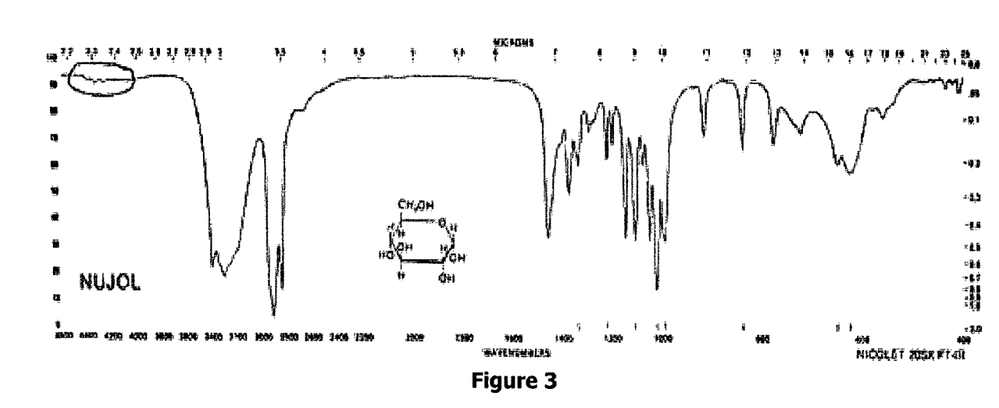
FIG. 3 (prior art) shows a Glucose spectrum over the mid IR, which exhibits a high spectral diversity, with more than twenty absorption peaks.
Figure 5:
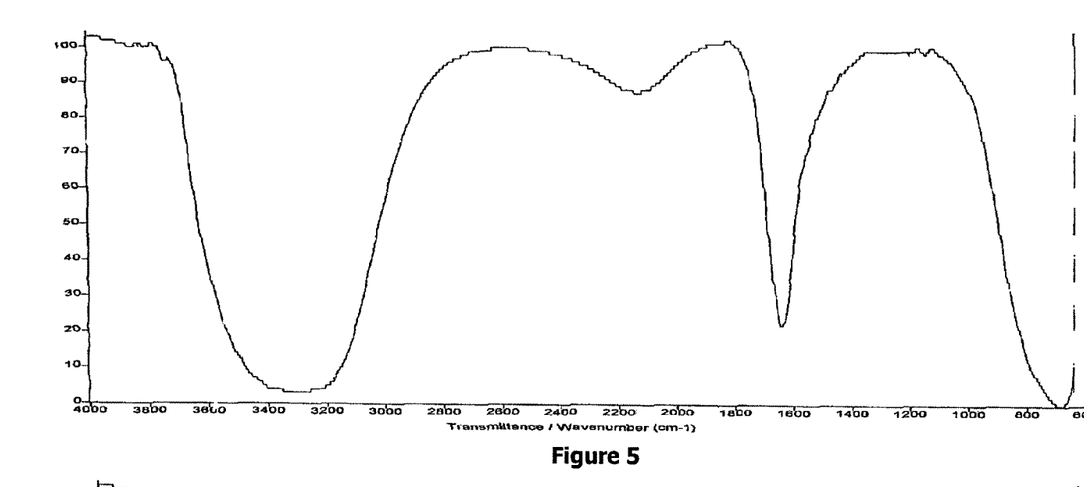
FIG. 5 (prior art) shows transmittance versus wave-number ($cm^{-1}$) for pure $H_2O$.
Figure 6:
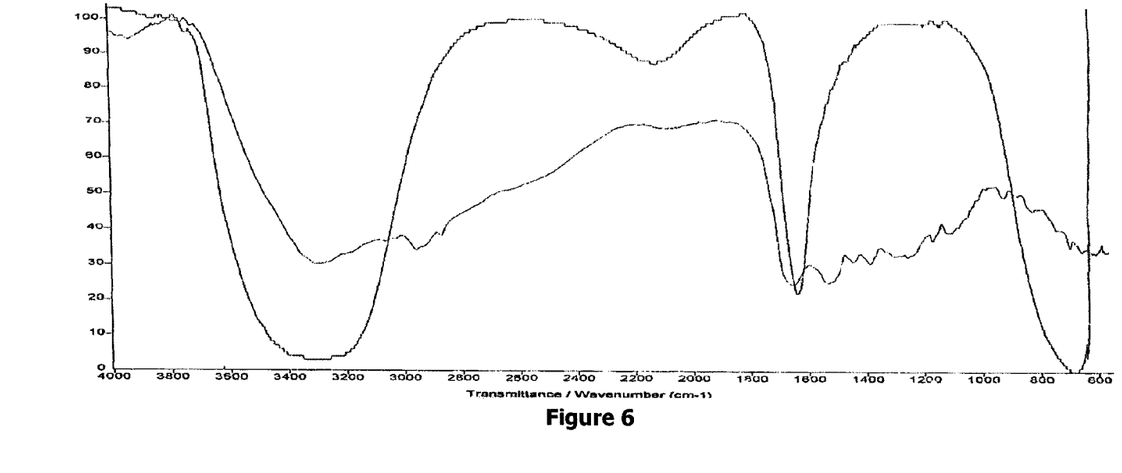
FIG. 6 (prior art) shows transmittance versus wave-number for Bovine Albumin superimposed on the transmittance versus wave-number ($cm^{-1}$) for pure $H_2O$ (cf.
Figure 7:
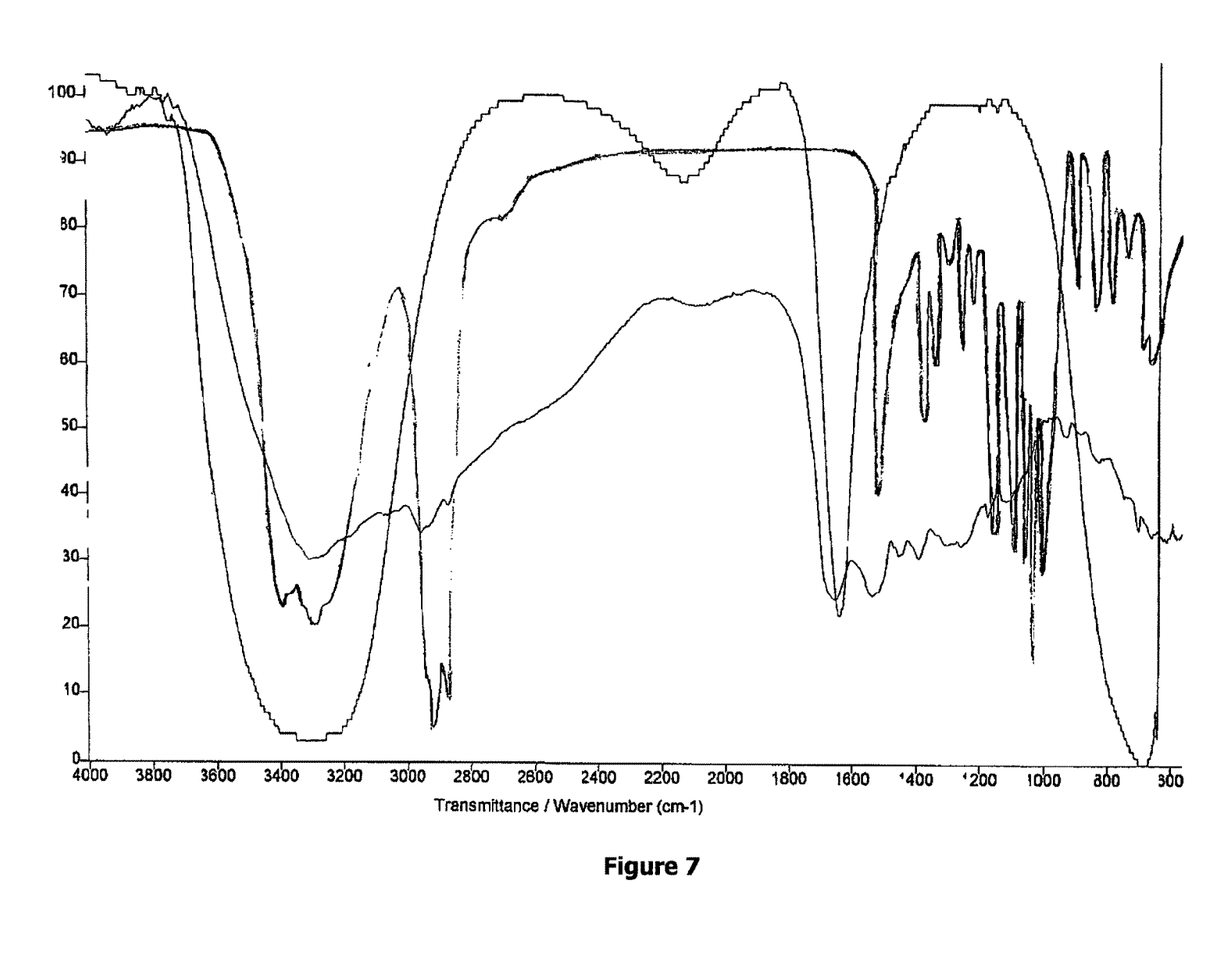
FIG. 7 ((prior art) shows transmittance versus wave-number for Bovine Albumin and for pure $H_2O$ superimposed on the transmittance versus wave-number ($cm^{-1}$) for Glucose (cf.

Glucose exhibits a high spectral diversity, since there are more than twenty absorption peaks over the mid IR. As shown in FIG. 3 (prior art) these absorption peaks are between 2700-3600 $cm^{-1}$ and 900-1500 $cm^{-1}$. The spectral absorbance of water in the mid IR (FIG. 5, prior art) does not obscure the 900-1500 $cm^{-1}$ spectrum and the spectral absorption of Bovine Albumin (plasma matrix) in the IR (FIG. 6, prior art) only partially obscures the 2700-3600 $cm^{-1}$ and 900-1500 $cm^{-1}$ spectrums that are two of the spectral bands rich in glucose absorbance (FIG. 7, prior art).

The rich mid-IR absorption texture of glucose and the diversity of the absorption bands for water and plasma matrix result in a potential glucose quantification, which will be significantly better than for that of the near-IR. The spectral diversity will also improve the discrimination potential of component regression techniques and provide more spectra for component regression analysis spectroscopy.

SUMMARY OF THE INVENTION

The invention includes a spectrometer, with no moving parts, utilizing a continuous wavelength filtering in the mid-infrared region and includes a sensitive thermal-based detecting array, providing transmission and/or reflection spectra over a range of wavelengths in the mid-IR region of electromagnetic radiation, identifying unknown samples by comparing the acquired spectra of the unknown sample with known mid IR spectra. The invention includes a very-low-thermal-mass emitting element which may be quickly pulsed to emit over a range of wavelengths including the mid-IR, providing for a differential measurement between background radiation and the radiation in the presence of the pulsed emission. The invention includes a variant where the material to be analyzed is contained within a holding "cell" which is transparent in the mid-IR. This invention is very light-weight, intrinsically rugged (no moving parts), and presents stable, accurate measurements in the presence of ambient thermal IR in the mid-IR regions, by differential measurements of a modulated, mid-IR thermal pulse extending from 2.5 to 12.5 µm.

This invention may measure other living tissue analytes, with the substitution of a particular analyte for glucose, and the substitution of relevant IR markers for the analyte, instead of the glucose IR markers, with any necessary changes in an interpretive, memory-based microcomputer program.

BRIEF DESCRIPTION OF THE DRAWINGS

For a more complete understanding of the present invention, and the advantages thereof, reference is now made to the following descriptions taken in conjunction with the accompanying drawings, in which:

FIG. 4);

FIG. 4—prior art);

DETAILED DESCRIPTION OF A PREFERRED EMBODIMENT

The following description is of the best mode presently contemplated for carrying out the invention. This description is not to be taken in a limiting sense, but is merely made for the purpose of describing the general principles of the invention. The scope of the invention should be determined with reference to the claims.

A preferred embodiment which we describe below can successfully measure glucose concentrations in the bloodstream (living tissue), in vivo, of humans and animals. It can also analyze other blood and bodily fluid analytes in a similar manner. Overall, the embodiment of the invention can measure simultaneously many analytes at once, by collecting all of these spectra simultaneously and using mid-IR multivariate analysis to disentangle the spectra.

By measurements in the mid-IR by a detector which utilizes (1) a very low thermal mass filament (FIG. 10, 101) to generate modulated IR radiation which passes through a relatively thin part of the living tissue (FIG. 10, 104) for example, for the human or animal body, such as an earlobe, and is spectrally separated (spectrally analyzed) by a continuously varying IR transparent set of quarter-wave plates, (FIG. 10, 102) and, which is then detected by a linear array of "hotplates" (FIG. 10, 103), where each "hotplate" is a flat, thermally conductive, absorptive (i.e., black) surface (FIGS. 14A, 14B, 402) which is flexibly connected to a substrate with differentially expanding bimetal "legs," (FIGS. 14A, 14B, 401) which vary the capacitance between the individual plates and a substrate, and which capacitance may be measured as part of a circuit, including by measuring the time to charge up the capacitor to a pre-specified voltage.

Figure 10:
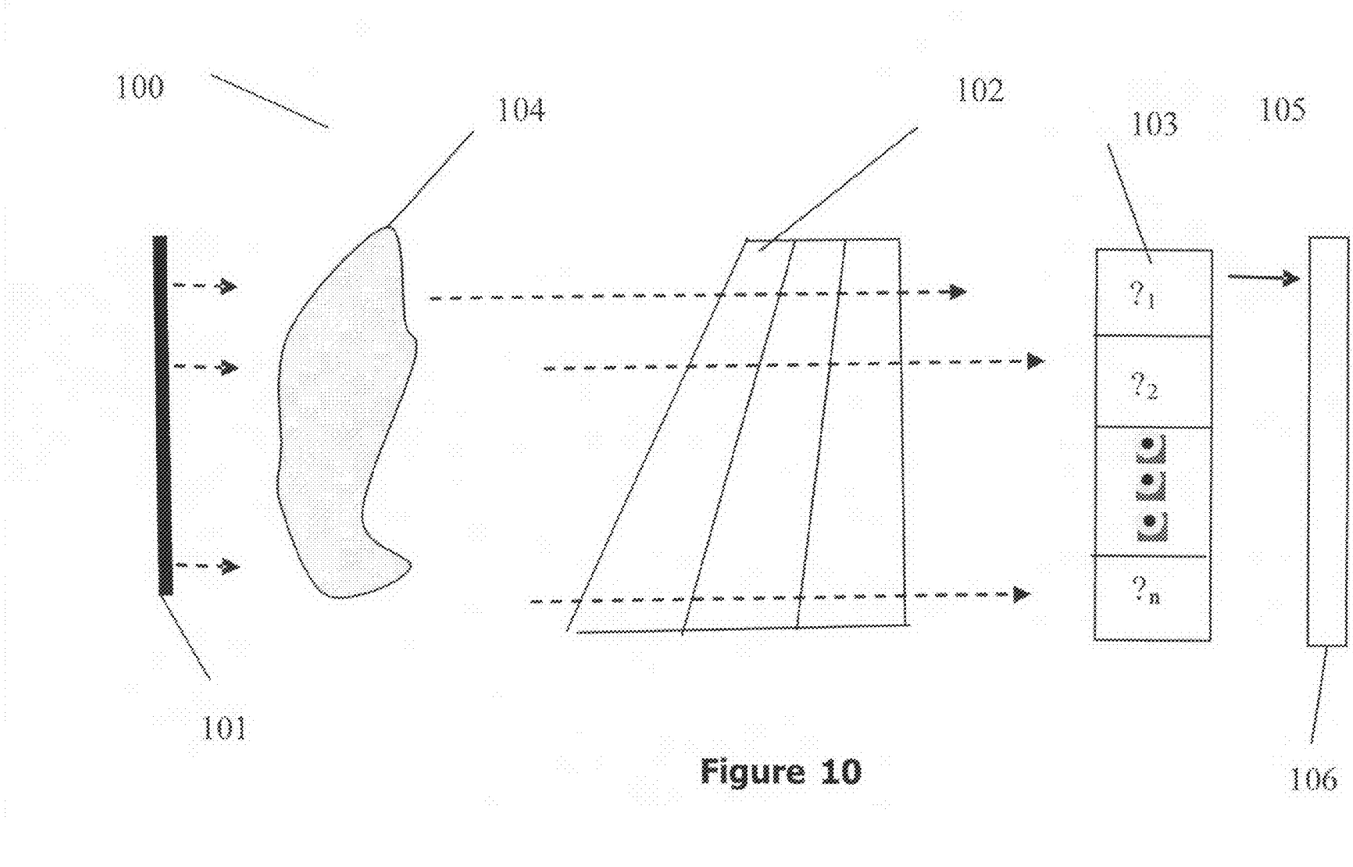
FIG. 10 shows an embodiment of the miniature mid-IR detector.

A preferred embodiment is shown in FIG. 10. The spectrometer 100 has three parts. The first part 101 is a low-mass micro-machined surface filament; the second part is the dispersive element 102, which is a large quantity of quarter wave plates, each plate asymmetrically enlarging from a quarter wave of 2.5 µm to a quarter wave of 12.5 µm; the third part is a linear array 103 with the detector elements thermally responsive such that, as they are heated, the capacitance between the plates (402, FIGS. 14A,B) and a substrate (105, FIGS. 10, 14A,B) decreases (because the heating cause the bimetallic "legs" to "rise up". The change in capacitance 105 is sensed by electronic circuit 106. In some embodiments, electronic circuit 106 is embedded in the substrate (i.e., monolithically integrated).

Figure 1:
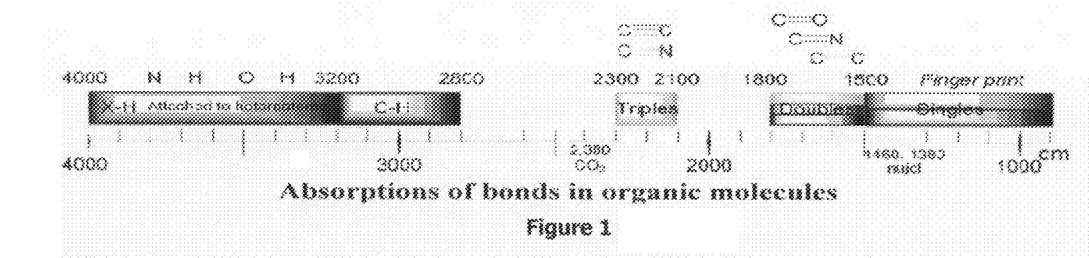
FIG. 1 (prior art) shows chemical bond responses to various IR wavelengths.

Surface micro machined radiator filaments FIG. 1, 101) may be fabricated with such low thermal mass that their temperature at all times correlate precisely with the current flowing through them. The naked micro filament also has no glass bulb envelope to be heated and cooled and that is opaque to radiation in the 2-13 µm band. The radiator elements can be heated and cooled in milliseconds, Un-cooled thermal IR detectors, such as the present invention 100, are sensitive to changes in illumination levels but not sensitive to absolute illumination levels thus the sensors typically require a modulated IR source.

In contrast to the present invention, historically, this modulation has been accomplished with mechanical choppers that consist of a drive motor, a rotating wheel to periodically interrupt the source-to-detector line of sight, and electronic pickups to synchronize the chopper and detector signals.

Choppers add the highest cost, largest size and greatest power consumption, and complexity to any product. Traditional incandescent specialty lamps and even ordinary panel lamps are not a good IR sources because they emit too wide a spectrum of light that is outside the desired measurement band producing "parasitic" heat that warms detectors, preamplifiers, and other components. The inefficiency of an incandescent bulb also dissipates excess power and heat and requires a higher drive power for the unit. This heat interferes with measuring the targeted spectrum and degrades the sensitivity and accuracy of the reading.

Electrical pulse shaping and current regulation rather than thermal mass control of miniature radiator means that it need only be powered for a short time and the low thermal mass 101 and high radiant output provides high temperature-slew rate with virtually no thermal hysteresis.

In the present invention, the instantaneous nature of the filament 101 output and the direct relationship with electrical drive power converts the difficult thermal stability problem into a straightforward matter of assuring electrical stability. Also, by concentrating electrical drive power into the wavelength range needed for the measurement, the micro radiator 101 assumes a portion of the task ordinarily performed by an interference filter to filter radiation outside the required wavelength.

The micro-machined radiator 101 integrates the traditional functions of discrete components—IR source emission, chopper modulation, and spectral filter—while minimizing size, power consumption, and heat dissipation and simultaneously maximizing performance.

Viewing FIG. 10, moving on to the dispersive section 102 of the spectrometer 100, one notes that to differentiate the rich spectral diversity of glucose, for example, a finesse of 2-3 nm (2 wave-numbers) is required—at least a 2000 bandwidth partition of the 2.5-12.5 µm spectrum.

Figure 13:
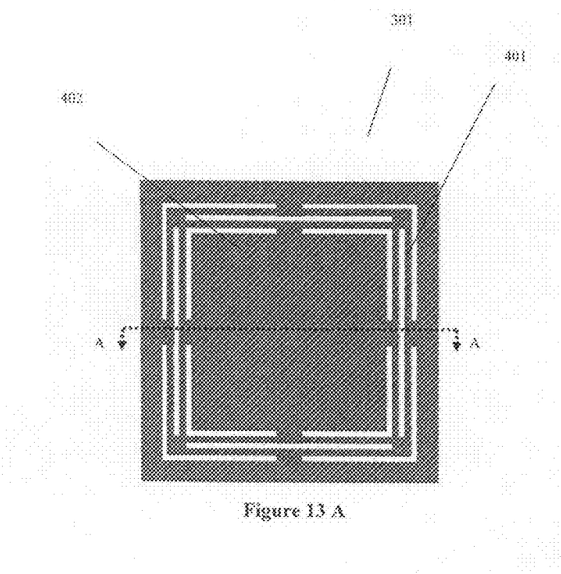
FIG. 13A shows a top view of a thermal plate detector ("hotplate")
FIG. 13B details of a thermal plate detector ("hotplare") cross-section BB of FIG. 13A.

A simplest frequency domain selection system is used, viz., a wedge filter (FIG. 10, 102) consisting of multi layers of low refractive index silicon dioxide and high refractive index silicon as illustrated in FIG. 13, 102).

Figure 11:
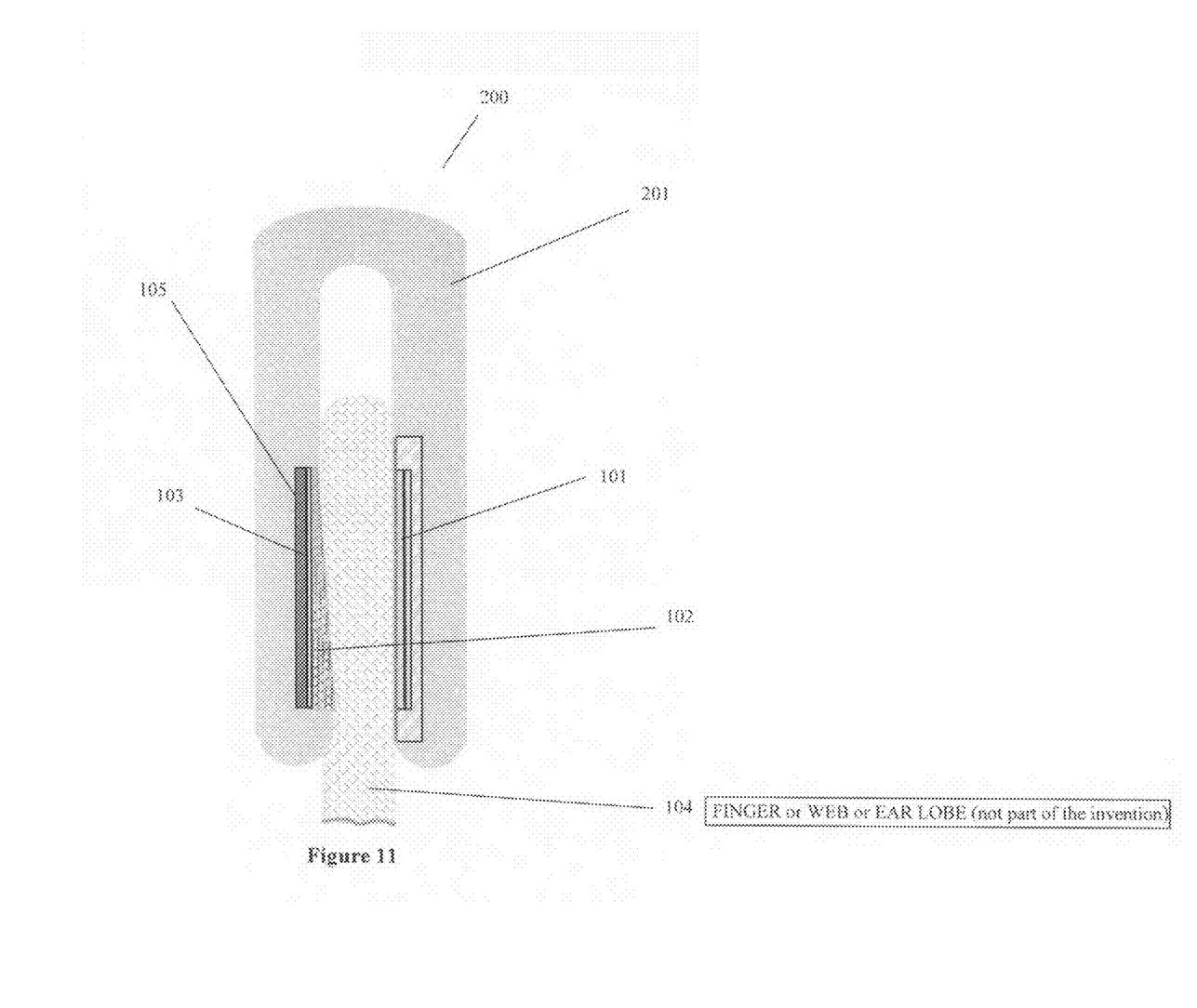
FIG. 11 shows an embodiment of the miniature mid-IR detector imbedded in a "clip-on" holder.
Figure 12:
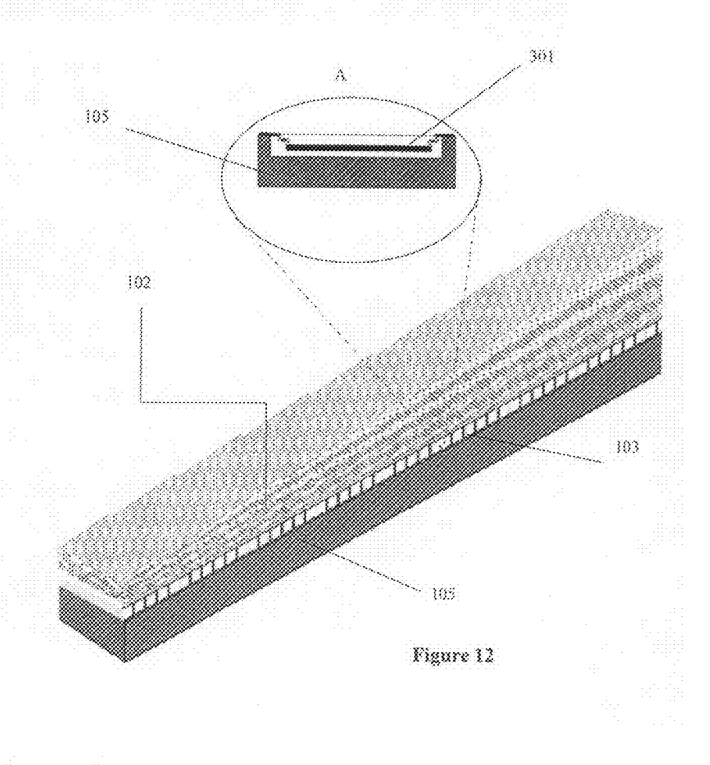
FIG. 12 shows a wedge interference filter with an INSERT A showing a blow-up of a thermal plate detector ("hotplate")

FIG. 11 shows a preferred embodiment 200 with the elements of FIG. 10, in a clip-on holding material 201. Show is the mid-IR pulsed source 101, the dispersive elements 102 and the detector array 103 against a silicon-based substrate containing electronics, known in the art. This FIG. 11 is schematic and does not show electronics and electronic information routing The thickness of these layers along the wedge are quarter the wavelength of interference filtering required at that spatial location. For example, at the beginning of the wedge where 2.5 µm transmission is required the thickness of dielectric layers would be 0.625 micron, while at the other end, where 12.5 µm is required, the thickness of the dielectric layers would be 3.125 µm.

There are many of these quarter wave plates, typically hundreds in a preferred embodiment.

FIG. 13 shows an insert A showing one of the "hot plate" elements 301 of the linear detector array 103, sitting on a part of the substrate 105.

Figure 14A:
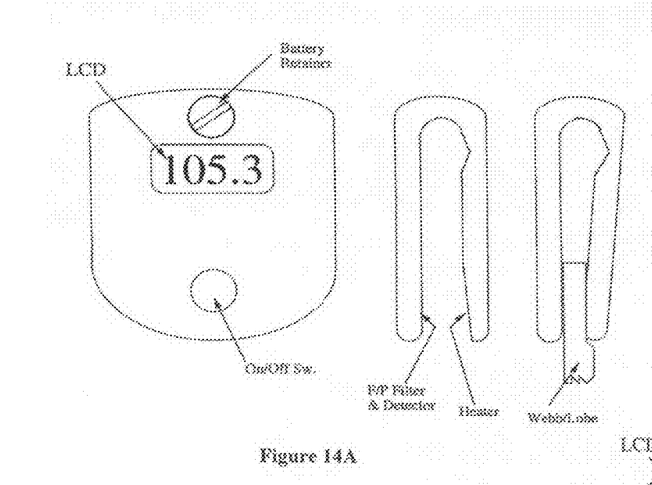
FIG. 14A shows the glucose detector set to be placed on an earlobe, or "web" between thumb and index finger.
Figure 14B:
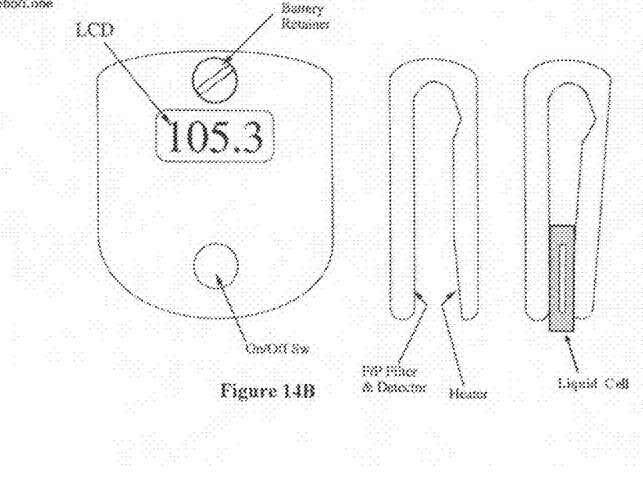
FIG. 14B shows the glucose detector set to be placed on an IR-transparent substance holder (e.g., saliva, urine)

A more detailed top view of a "hot-plate" element is shown in FIG. 14A, where the arrangement of the bimetallic "crab-legs" 401 are shown in relation to the blackened, conductive top 402. The cross section AA of FIG. 14A is shown in FIG. 14B. The "hot-plate" element 301 has a top plate and bimetallic "crab-legs" 401. When the top 402 is heated, the heat is thermally conducted from the top 402 to the bimetallic "crab-legs" 401, which legs 401 undergo expansion such as to raise the top 402 away from the substrate 105. This results in a relative change in the local capacitance between the top 402 and the substrate 105, which capacitive changes is measured by electronics in the silicon (or similar) based electronics, known in the art.

Conventional thermal IR detection is by means of photo diodes, thermopiles or thermo resistive devices. The sensitivity and even the capacity for quantification of radiation of photodiodes and thermopiles is related to the absolute temperature of the sensor, while the temperature sensed by thermo resistive elements is contaminated by the energy that is dissipated in device while making a resistive measurement.

Bimorph (bimetallic, usually) flexure translation, on the other hand, is dependent on its absolute temperature. Bimorphic temperature measurement thus becomes a displacement measurement that does not involves any heat flux measurement mechanisms.

A radiative thermal sensor requires a high emissivity surface to absorb (or emit) the major portion of IR radiation, a low thermal capacity to transduce the radiative flux to temperature, vacuum environment to eliminate convective transfer and structural isolation to prevent conductive transfer. A bimorphic deflection is related to the disparity in thermal coefficients of expansion of the 'bi' materials of the laminated flexure and the temperature of flexure. The capacitance measurement is the simplest means of non-contact sensing of proximity and the most sensitive of proximity discrimination is resolving the separation between parallel electrodes.

A significant innovation in the realization of a bimorphic IR detector is the architecture for a sensitive deflection measurement.

Extremely thin film membranes have low thermal capacity; an eight crab-leg 401 flexure facilitates 'parallel' plate deflection; a high emissivity coating on membrane maximizes IR absorption; high thermal conductance material for membrane and flexures (preferably diamond film) minimizes the time constant; metal film beneath the flexure (having a higher thermal coefficient of expansion than the flexure material) produces bimorphic deflection; a metal substrate 105 spaced a small distance below the flexure suspended membrane provides gap' sensing means.

As known in the art, capacitance is most directly measured and precisely digitized with a current mirror arrangement to charge up a capacitor to a reference potential and timing how long this takes. The magnitude of the constant current; value of reference potential; and the frequency of the counter clock would be selected to generate a sixteen-bit count for the maximum capacitance encountered.

The thermal capacity of the absorption platform 401 and the thermal conductance of platform 402 and flexures 401 is targeted to a 15 millisecond time constant.

As an example, as known in the art, the substrate metal plate 105 would use metal laid out with near 100% fill-factor and connected to underlying electronic circuits through metal via plugs. High sensitivity capacitance detection requires that the top metal electrodes are separated from other structures by a thick (~1.5 µm) dielectric and through a careful layout minimizing coupling capacitance. The bottom metal of all the flexured platforms would be contiguous over the whole array and connected to 'ground'. Useable materials (known in the art) include Polycrystalline Diamond: Thermal expansion coefficient $1.1 \times 10^{-6}$/K, Thermal Conductivity 20 W/cm-K, Tensile strength >1.2 GPa. Thermal expansion coefficients for BiMorph metals: Cesium $97 \times 10^{-6}$/K, Potassium/Gold (2/1)~$60 \times 10^{-6}$/K, Mercury/Gold (2/1)~$45 \times 10^{-6}$/K, Lithium/Gold (2/1)~$35 \times 10^{-6}$/K, Zinc $30 \times 10^{-6}$/K, Tin $22 \times 10^{-6}$/K.

Sample electronics, known in the art, include substrate metal plates (pixelated) beneath these flexured platforms are periodically reset by discharging them to ground potential. This reset is the epoch for connecting each metal plate (capacitor) with its current mirror and voltage comparator that 'gate' the system clock to respective counters (one per pixel). The leading edge of capacitor reset command evokes the parallel transfer of all counter registers into segments of large serial shift register and the trailing edge of the reset command clears all the counter registers.

Measurement of In Situ In Vivo Blood Sugar Levels.

Figure 15A:
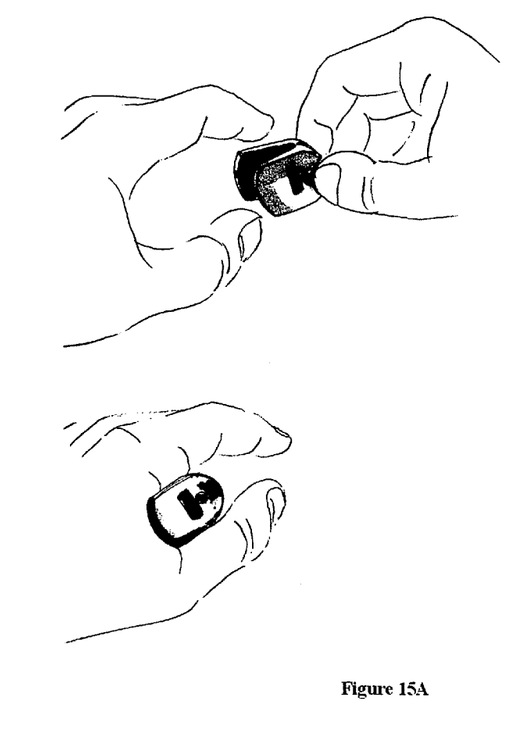
FIG. 15A shows the mid-IR spectrometer as a wearable glucose detector.
Figure 16:
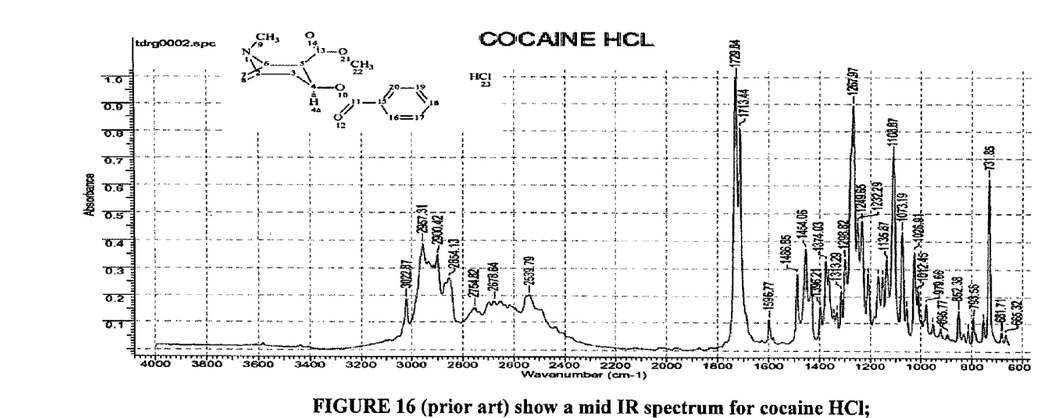
FIG. 16 (prior art) show a mid IR spectrum for cocaine HC.

To accomplish this, a direct short transmission path length and high absorption specificity may be utilized. The ex vitro measurements are therefore typically made across the tips of fingers, through the "web" between thumb and forefinger (FIG. 15A) or through an ear lobe (FIGS. 16A,B).

Utilizing one or more "between-toe" "webs" on the feet, as well as "earrings," may provide attachment for a continuously wearable glucose detector. An illustration of how a web or lobe device might direct a micro-machined IR source (heater) through a body and on to a dynamic IR filter and detector can be seen in FIG. 15A.

Figure 15B:
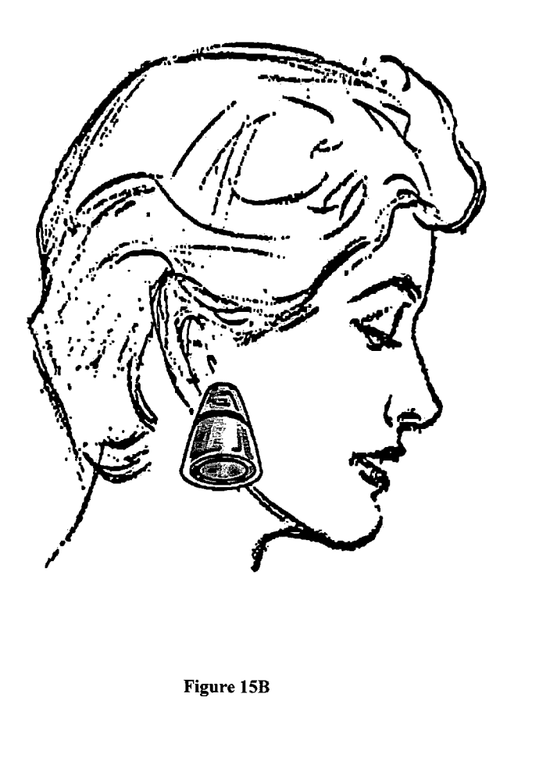
FIG. 15B shows the clip-on "earrings" mid-IR spectrometer.

For use with body fluids such as saliva and urine, FIG. 15B illustrates the use of a work-harded mid-IR transparent "cell" which is made of a AgClBr material.

Figure 17:
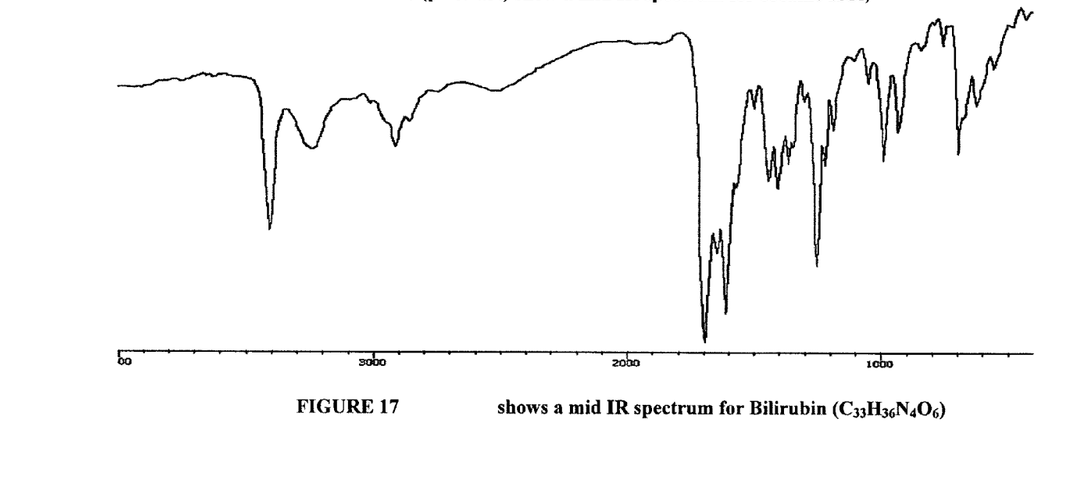
FIG. 17 shows a mid IR spectrum for Bilirubin ($C_{33}H_{36}N_4O_6$).

Additional analytes which are examples only, include the forensic valuable Cocaine (FIG. 16) and Bilibubin (FIG. 17), which is an important health analyte.

Figure 8:
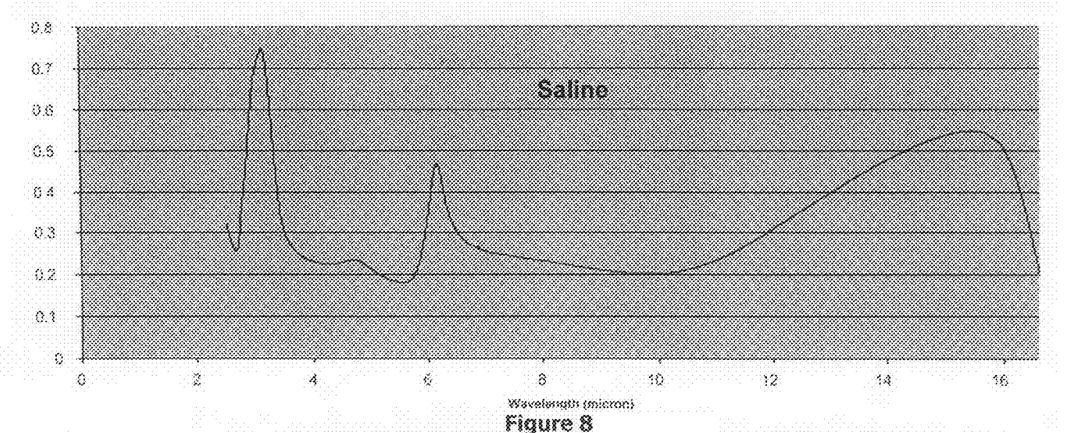
FIG. 8 (prior art) shows absorption spectra for Saline solution.
Figure 9:
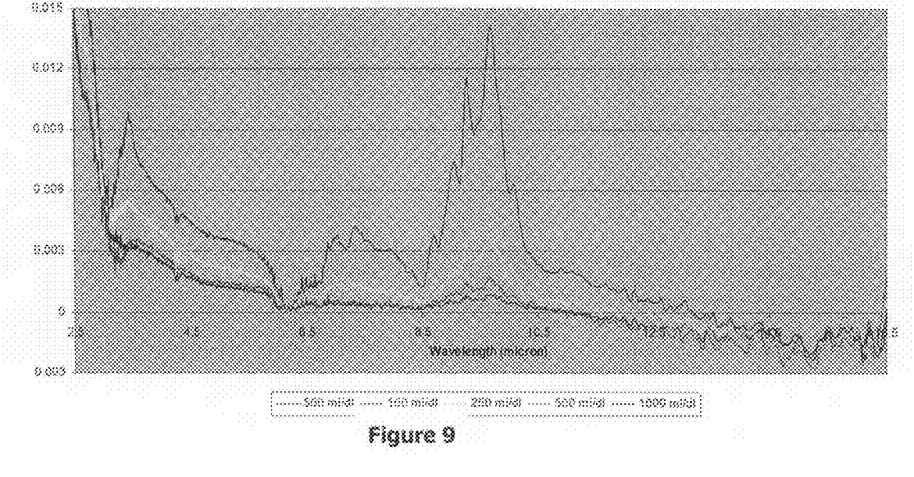
FIG. 9 shows absorption spectra for Glucose in Saline solution.

A laboratory broadband IR spectrometer (cooled detector) measured the absorption spectra of Saline solution over 2.5 µm m to 16.5 µm range of wavelengths. The results are plotted in FIG. 8 (prior art). The same instrument measured the absorption spectra of various concentrations of glucose in Saline solution. The results for the specific concentrations of glucose of 50, 100, 250, 500 and 1000 ml/dl are plotted on a common graph (FIG. 9, prior art). The rich glucose absorption texture between 3.35 and 3.75 µm and between 6 and 10.5 µm (FIG. 3, prior art) are clearly demonstrated in the low Saline absorption bandwidths between 3.5 and 5.5 µm and particularly between 7.5 and 11 µm. Template fitting of these differential spectra across the 3 to 11 µm results in less uncertainty than over any narrower bandwidth fitting and possibly with sufficient precision in quantification to resolve glucose concentration to the ml/dl level.

EXAMPLE

The 1500 cm−1 absorption peak for glucose (FIG. 4, prior art) and the 1650 cm−1 absorption peak for water are discernible at body temperatures, and will enhance the precision of component regression.

The glucose measurement procedure would commence when the unit is turned on followed by a full spectrum measurement (simultaneous) at two radiator temperatures to calibrate the detector measurement chain. Subsequently, when a hand web or ear-lobe is clamped in the device, these same spectrum will be taken again for both two radiator temperatures.

Microcontroller

These procedures are orchestrated by a dedicated microcontroller that also undertakes component regression analysis against a priori absorption spectrum templates for the aqueous matrix and the glucose. The relative magnitude of absorbance for the various glucose spectral bands will enable quantification of the amount of glucose present and its display on a small LCD (FIG. 14).

Communication The spectrometer applied to glucose (glucometer) may communicate with an insulin pump via a wire or by a wireless intermittent, low power transmitter.

Calibration The calibration of the spectrometer is done over a large number of potentially present analytes and the spectra are assimilated into a detection profile which can be downloaded in a small computer/electronic unit, known in the art, attachably ot integrally part of the spectrometer, or located nearby the spectrometer.

Figure 14C:
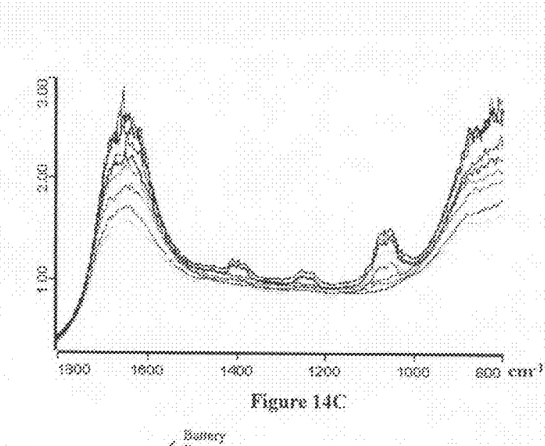
FIG. 14C shows the saliva and saliva related mid-IR spectra.

Oral applications Saliva can be introduced into the sample or specimen cell (FIG. 14B). Various mid-IR spectra for saliva is shown in FIG. 14C. It is expected to detect the state of the health of the mouth. This includes identification of the bacterial and viral species contained in a person's mouth, including HIV, HSV1, HSV2, EBV, CMV, *Prevotella intermedia, Porphyromonas gingivalis, Streptococcus mutans*, etc. Identification and quantification could be achieved by assessing the antigens or unique molecules specific for the pathogens. These areas of dentistry are largely untouched at this moment and we consider this to have an immense potential in provision of dental services.

Hyperspectral The dispersive elements may be enlarged perpendicular to the linear array, and the linear array may be formed instead as a two-dimensional array. Consequently, if the input to the dispersive elements, is, for example, by means of a lens viewing a two-dimensional surface emitting in the mid-IR, this hyperspectral variant of a preferred embodiment is included in the invention.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in It is claimed that:

1. An apparatus for detecting mid-IR spectra, comprising:
   a surface micro-machined low mass thermal emitter wherein the emitter is electrically pulsed and emits electromagnetic radiation including the mid-IR, 2.5 to 12.5 µm;
   a set of quarter-wavelength plates of a mid-IR transmitting material wherein the thickness of the plates progressively increases from a quarter wavelength of 2.5 µm on a first end of the set of quarter-wavelength plates to a quarter wavelength of 12.5 µm at a second end of the set of quarter wavelength plates wherein the set of plates acts as a dispersive spectroscope element in the mid-IR;
   a set of detector elements wherein each element responds to heating at its location wherein each element's location corresponds to a given member of a set of dispersed radiation in the mid-IR wherein a heated element is disposed to rise from a substrate when heated; and
   wherein each of the set of detector elements forms a capacitor with the substrate and its energy absorption at its dispersed wavelength location is measurable wherein the capacitance relative to the substrate is changed.

2. The apparatus of claim 1, further comprising:
   detector elements having bimetallic legs wherein the heating of a detector element blackened flat plate absorbs mid-IR radiation and transfers energy in a thermal form by conduction to its legs wherein the bimetallic legs are disposed to move so as to lift the blackened electrically and thermally conductive plate away from the substrate.

3. The apparatus of claim 1, further comprising:
   the substrate on which the detector elements are attached, the substrate containing a plurality of embedded electronic circuits; and the embedded electronic circuits disposed to monitor and transmit capacitive changes from a changed height above the substrate of a detector plate element.

4. An apparatus for spectrally analyzing mid-IR electromagnetic radiation, comprising:
   a surface micro-machined low mass thermal emitter wherein the emitter is electrically pulsed and emits electromagnetic radiation including the mid-IR, 2.5 to 12.5 µm; and a set of quarter-wavelength plates of a mid-IR transmitting material wherein the thickness of the plates progressively increases from a quarter wavelength of 2.5 µm on a first end of the set of quarter-wavelength plates to a quarter wavelength of 12.5 µm at a second end of the set of quarter wavelength plates wherein the set of plates acts as a dispersive spectroscope element in the mid-IR; and
   a set of detector elements wherein each element responds to heating at its location wherein each element's location corresponds to a given member of a set of dispersed radiation in the mid-IR wherein a heated element is disposed to rise from a substrate when heated; and give rise to a measurable change in relative capacitance.

5. The apparatus of claim 4, further comprising: detector elements for detecting a plurality of energies at different mid-IR wavelengths emerging from the set of quarter wavelength plates.

6. A method for measuring spectra in the mid-IR, comprising:
   emitting a pulse of mid-IR containing electromagnetic radiation by electrically pulse heating a very low mass surface micro-machined metal element;
   dispersing the mid-IR electromagnetic energy into varying wave-lengths by a set of quarter wave filter elements;
   forming the dispersing set of quarter wave filter elements wherein a first end of the elongated quarter wavelength filters starts as a quarter wave-length thickness of the wave-length 2.5 µm and wherein a second end of the elongated quarter wave-length filters starts as a quarter wave-length thickness of the wavelength of 12.5 µm; and wherein the thicknesses of the quarter wave filter elements vary continuously between these two specific end point quarter wave-lengths;
   detecting the energy in the various dispersed wave-lengths by a detector;
   varying the capacitance of the detector using a blackened thermal and electrically conducting plate supported by bimetallic legs so as to vary the capacitance of the detector by varying the distance between a substrate and the blackened conducting plate according to the energy transferred to the bimetallic legs;
   disposing the legs of the detector wherein the shape of the legs responds to heating so as to lift up the detector plate; and
   measuring the capacitive change by electronics embedded in the substrate.

7. The method of claim 6, further comprising:
   communicating the results of the measurement of the spectral energies by an embedded transmitter;
   controlling an insulin pump according a program stored on an electronic memory device wherein the insulin dosage is according to medical advice.

8. The method of claim 6, further comprising:
   communicating the results of the measurement of the spectral energies by activating a cell phone;
   collecting the measurement data in a remote central data collection place.

9. The method of claim 6, further comprising:
   measuring a set of analytes simultaneously present in a mid-IR responsive sample;
   utilizing pre-measured individual spectra;
   pre-analyzing the mixtures of different analytes according to multi-variate analysis;
   retaining a combination template in an electronic memory;
   comparing the results of measuring the various energies present at different wavelengths; and
   estimating the composition of the unknown sample by utilizing combination templates.

10. An apparatus for detecting mid-IR electromagnetic radiation, comprising:
    detector elements having bimetallic legs wherein the heating of a detector element blackened flat plate absorbs mid-IR radiation and transfers energy in a thermal form by conduction to its legs wherein the bimetallic legs are disposed to move so as to lift the blackened electrically and thermally conductive plate away from a substrate, and wherein the bimetallic legs comprise a first material that is a high thermal conductance material, and further wherein the bimetallic legs and the substrate are thermally coupled;

the substrate on which the detector elements are attached, the substrate containing a plurality of embedded electronic circuits; and the embedded electronic circuits disposed to monitor and transmit capacitive changes from a changed height above the substrate of a detector plate element.

11. The apparatus of claim 10, further comprising:
a surface micro-machined low mass thermal emitter wherein the emitter is electrically pulsed and emits electromagnetic radiation including the mid-IR, 2.5 to 12.5 µm;
a set of quarter-wavelength plates of a mid-IR transmitting material wherein the thickness of the plates progressively increases from a quarter wavelength of 2.5 µm on a first end of the set of quarter-wave plates to a quarter wavelength of 12.5 µm at a second end of the set of quarter wavelength plates wherein the set of plates acts as a dispersive spectroscope element in the mid-IR.

12. The apparatus of claim 10, further comprising:
a set of quarter-wavelength plates of a mid-IR transmitting material wherein the thickness of the plates progressively increases from a quarter wavelength of 2.5 µm on a first end of the set of quarter-wave plates to a quarter wavelength of 12.5 µm at a second end of the set of quarter wavelength plates wherein the set of plates acts as a dispersive element in the mid-IR;
an imaging lens in front of the set of quarter-wavelength plates;
the set of quarter wave plates extending in a second direction, perpendicular to both a linear detector array and a line from the center of the lens to a center of a two-dimensional detector array wherein an image formed by an imaging lens onto the two-dimensional detector array wherein the apparatus performs as a hyperspectrometer.

13. The apparatus of claim 12, further comprising:
a detection apparatus for bacteria residing in a mouth of a human being, said human explicitly not being part of the invention.

14. The apparatus of claim 12, further comprising:
a detection apparatus for viruses residing in a mouth of a human being, said human explicitly not being part of the invention.

15. The apparatus of claim 12, further comprising:
a detection apparatus for pathogen antibodies residing in a mouth of a human being, said human explicitly not being part of the invention.

16. The apparatus of claim 12, further comprising:
a detection apparatus for pathogen-specific organic molecules residing in a mouth of a human being, said human explicitly not being part of the invention.

17. The apparatus of claim 12, further comprising:
a detection apparatus for cocaine.

18. The apparatus of claim 12, further comprising:
a detection apparatus for glucose.

19. The apparatus of claim 12, further comprising:
a detection apparatus for bilirubin.

20. An apparatus for detecting mid-IR spectra, comprising:
a surface micro-machined low mass thermal emitter wherein the emitter is electrically pulsed and emits electromagnetic radiation including the mid-IR, 2.5 to 12.5 µm;
a set of quarter-wavelength plates of a mid-IR transmitting material wherein the thickness of the quarter-wavelength plates progressively increases from a quarter wavelength of 2.5 µm on a first end of the set of quarter-wavelength plates to a quarter wavelength of 12.5 µm at a second end of the set of quarter-wavelength plates wherein the set of quarter-wavelength plates acts as a dispersive spectroscope element in the mid-IR;
a set of detector elements wherein each element responds to heating at its location wherein each element's location corresponds to a given member of a set of dispersed radiation in the mid-IR wherein a heated element is disposed to rise from a substrate when heated; and the displaced heated element forms a capacitor with the substrate and its energy absorption at its dispersed wavelength location is measurable wherein the capacitance relative to the substrate is changed;
wherein each of the detector elements comprises bimetallic legs wherein the heating of a detector element blackened flat plate absorbs mid-IR radiation and transfers energy in a thermal form by conduction to its legs wherein the bimetallic legs are disposed to move so as to lift the blackened electrically and thermally conductive plate away from the substrate; and
the substrate, the substrate comprising the detector elements and a plurality of embedded electronic circuits, each of the embedded electronic circuits being disposed to monitor and transmit capacitive changes from a height change of one of the detector plate elements above the substrate.

* * * * *